United States Patent [19]

MacLean et al.

[11] Patent Number: 4,496,347

[45] Date of Patent: Jan. 29, 1985

[54] FEEDING TUBE STYLET

[75] Inventors: David MacLean; Robert B. Edwards, II, both of Libertyville, Ill.

[73] Assignee: Viridian, Inc., Wheeling, Ill.

[21] Appl. No.: 422,564

[22] Filed: Sep. 24, 1982

[51] Int. Cl.³ .................... A61M 25/00

[52] U.S. Cl. .................... 604/164; 128/657

[58] Field of Search .................... 604/164–170, 604/280; 128/672, 657

[56] References Cited

U.S. PATENT DOCUMENTS

| | | | |
|---|---|---|---|
| 3,395,711 | 8/1968 | Plzak, Jr. | 128/200.26 |
| 4,020,829 | 5/1977 | Willson et al. | 128/657 |
| 4,257,421 | 3/1981 | Beal | 128/657 |
| 4,388,076 | 6/1983 | Waters | 604/165 |

*Primary Examiner*—Stephen C. Pellegrino

*Attorney, Agent, or Firm*—Robert E. Wagner; Linda A. Kuczma

[57] ABSTRACT

A stylet to be used in combination with a feeding tube assembly for administration or aspiration of fluids to a patient comprising a wire with an elongated loop of variable length and width at its distal end. The width of the loop may be adjusted so as to be greater than the diameter of any apertures in feeding tubes thereby preventing the stylet from exiting the tube assembly and minimizing the possibility of injury to a patient during stylet intubation.

2 Claims, 9 Drawing Figures

FEEDING TUBE STYLET

DESCRIPTION

1. Technical Field

The present invention relates generally to the intubation of patients for the internal administration of fluids to patients, detection and treatment of medical complications, and to the decompression of the stomach and duodenum and in particular, to an improved stylet for the insertion of tube assemblies therefor.

2. Background of the Invention

During the medical treatment of some patients, it becomes necessary for a patient to undergo enteric therapy by administering medical preparations and fluid nutrients through a flexible feeding tube or catheter having a very small cross sectional diameter. Feeding tubes are usually inserted nasally, but may also be inserted orally. Nasally inserted tubes are commonly referred to as nasogastrointestinal tubes and are inserted into a nostril, guided through the nasopharynx, through the oropharynx and into the esophagus. The tube advances into the patient's stomach or duodenum either by peristaltic movement, i.e., peristaltic intubation, or by the use of an internal guide or stylet, i.e., stylet intubation. The stylet is generally formed from a piece of wire at least as long as the length of the tube, and is usually inserted into the proximal end of the feeding tube prior to introduction into the patient. The person inserting the guide places the tube into the patient's intestinal tract by carefully pushing the tube along the aforementioned path.

In their most common form, prior art stylets are slender surgical probes constructed of wire and generally formed from a single strand of wire with a small metal bead-like shape welded to one end. The cross sectional diameter of the stylets usually are significantly less than the cross sectional diameter of the feeding tube into which they are inserted. The beaded end of one such stylet is inserted into the feeding tube to facilitate intubation of patients who are unable to aid the progression of the tube into the gastrointestinal tract by swallowing or voluntary perstaltic movement.

Typically, feeding tubes are necessary for patients who are unable to swallow or are having difficulty masticating, but nevertheless have functioning gastrointestinal tracts. These so-called feeding tubes are also used to assess internal functions, detect medical complications, treat medical problems, administer medications and to decompress or reinflate the stomach and duodenum postoperatively to prevent the effect of diminished or complete absence of peristalsis either during or subsequent to surgery.

Feeding tubes have been introduced into the market constructed of either polyurethane or silicone rubber. These tubes can remain inserted in the patient for longer periods of time due to their decreased size and increased resistance to degradation by gastric acids.

In certain common forms, these prior art tubes possess one of two basic weight containing structures at their distal end. These structures aid in the gravity placement of the tube, the prevention of involuntary regurgitation of the tube and assist in the peristaltic movement of the tube into the gastrointestinal tract.

The weights are generally positioned in either of the following manners. In the first version, an elongated bullet-shaped tip, sufficiently larger in cross sectional diameter than the tubing, and filled with liquid mercury, is located at the distal end of the tube. This configuration provides maximum weight and a sizeable protrusion which facilitates peristaltic intubation. Fluids conducted through the tube exit the tube through apertures in the tube wall positioned proximal to the tip.

To ensure safe placement of the tube in the stomach or duodenum during stylet intubation, the stylet must be properly inserted in the enclosed space between the aperture closest to the distal end of the tube and the end of the tube lumen.

However, the major disadvantage encountered with the above-described prior art stylets is the risk of internal injury to the patient should a stylet exit the tube through an outlet during stylet intubation.

The second prior art version possesses a weighted slenderized tip, containing mercury, which is of the same cross sectional diameter as the tube itself. This slenderized configuration alleviates the problems encountered with the insertion of the bullet-shaped tip discussed above. This slenderized tube has several apertures near its distal end and requires stylet intubation since the smooth even-diametered tube and tip shapes provide no protrubances necessary for implementing peristaltic action. Therefore, despite the weighted distal end, the patient remains unable to aid the progression of the tube by swallowing, and passage from the stomach to the duodenum by peristalsis is impeded, further inhibiting the effectiveness of this type of tube.

Hence, a need existed for a feeding tube and stylet system which could be inserted with minimal discomfort to the patient and without the risks commonly associated with stylet intubation.

SUMMARY OF THE INVENTION

According to the present invention, a stylet to be used in connection with a feeding assembly for the administration of fluids to patients, detection and treatment of medical complications and decompression of the stomach and duodenum of a patient, has been developed which alleviates the risks presented during insertion of prior art tubes assemblies.

Generally, the present invention embodies a stylet to be used for the insertion of a feeding assembly. The preferred feeding assembly is comprised of a flexible tube with an internally weighted guide tip located at the distal end and a bead-like bolus located proximal to the guide tip. The stylet is comprised of a single or stranded wire which has been bent in half, the arms of said wire being twisted about each other to form a double helix. The arms of the strand of wire are twisted to form an elongated loop of variable size.

The guide tip of the preferred assembly has the same, or slightly less cross sectional diameter than the cross sectional diameter of the tube. The guide tip is designed for simpler and less painful intubation of patients as will be later explained. Cylindrical tungsten segments, or segments of similar material, provide the necessary weight and rigidity for insertion. The tungsten contained in the guide tip is non-toxic to the patient and resistant to degradation by gastric acids.

The distal portion of the preferred tube assembly contains a bead-like bolus located proximal to the guide tip and made from essentially inert plastic or like material. Unlike prior art assemblies, the bolus, rather than the tube, contains lateral apertures which permit the release or passage of fluids from the tube. Additionally, the bolus provides a rigid housing for the distal end of the stylet permitting safe placement of the tube during stylet intubation. Due to its location behind the guide tip, the bolus passes easily and without discomfort through the nasal passages.

The greatest width of the elongated loop, located at the distal end of the stylet, is almost as large as the cross sectional diameter of the tube lumen and/or the bolus housing described above, thereby prohibiting the unintentional exit of the stylet from the tube lumen or bolus housing. The present invention may also be used in the insertion of prior art feeding assemblies. The width of the elongated stylet loop can be greater than the major diameter of the apertures thereby inhibiting the stylet from exiting the tube. The elongated loop also allows for the free flow of liquid from the bolus or the tube while the stylet remains inserted in the tube assembly.

The present invention is further described and disclosed through a preferred embodiment presented in the drawings and set forth below in the written description.

DETAILED DESCRIPTION

Figure 1:
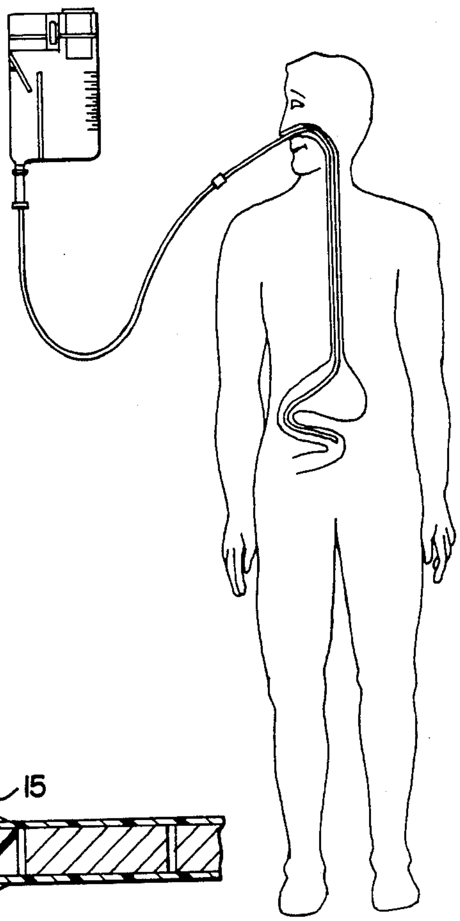
FIG. 1 is an illustrative diagram showing the placement and insertion of a feeding tube assembly in combination with an enteric feeding bag.

Referring now to the drawings, FIG. 1 illustrates the insertion path and placement of a feeding tube assembly. More specifically, FIG. 1 illustrates the nasal insertion of a feeding tube assembly, said feeding assembly shown in combination with an enteric feeding bag. Subsequent to insertion of the feeding assembly into the nasal cavity of the patient, the feeding assembly passes through the back of the throat or pharynx of the patient, into the esophagus. Peristaltic action or insertion with a stylet progresses the feeding assembly to the desired location, usually the stomach, or the duodenum, more commonly known as the intestinal tract.

Figure 2:
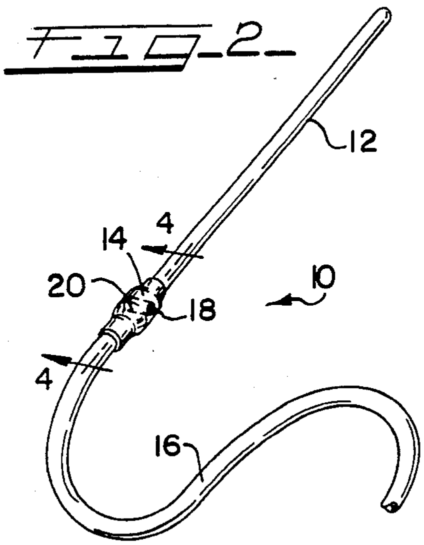
FIG. 2 is a detailed perspective view of a feeding tube assembly illustrating the preferred guide tip and irrigation or aspiration means.
Figure 4:
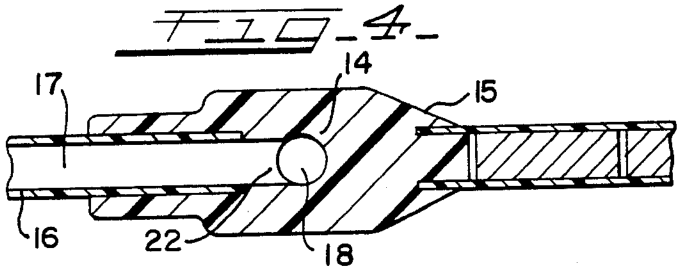
FIG. 4 is a detailed vertical cross sectional fragmentary view of the distal end of a feeding tube assembly taken along line 4—4 in FIG. 2, including part of the guide tip, and bolus.
Figure 5:
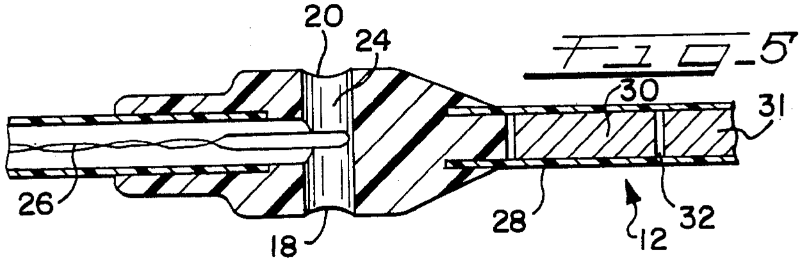
FIG. 5 is a detailed horizontal cross sectional fragmentary view of the distal end of the tube assembly shown in FIG. 4, showing the subject invention inserted in said tube.

FIG. 2 illustrates a preferred feeding assembly, generally referenced by the numeral 10, for use with the present invention. The feeding assembly 10 shown in FIGS. 2, 4 and 5 is an improvement over the prior art feeding assembly 34 shown in FIGS. 3, 7, 8, 9 and is the subject of a separate patent application entitled Improved Feeding Tube Asssembly, Ser. No. 422,565, filed on Sept. 24, 1982, in the names of Robert B. Edwards II and David G. Quinn. Feeding tube assembly 10 is of a linear tubular shape generally used in the art, and includes a guide tip 12 and hollow tube 16 which are manufactured from polyurethane or silicone rubber. Assembly 10 further includes a smooth, contoured partially hollow bolus 14 having openings 18 and 20 to allow for the selective exit or entry of fluids into hollow tube 16. The bolus 14 is located between the guide tip 12 and tube 16 and is made of a rigid but somewhat compliant plastic or similar material. The bolus 14 possesses a larger cross-sectional diameter than the cross-sectional diameter of tube 16. This increased cross-sectional diameter provides a necessary protrubance for peristaltic action to occur, thereby facilitating peristaltic intubation of a patient.

Guide tip 12 is of a generally tubular shape and possesses a diameter smaller than the diameter of the bolus 14. Preferably, guide tip 12 possesses a diameter which is less than or equal to the diameter of the tube 16. The portion of the bolus 14 distal to channel 24 is smoothly and gradually tapered to the diameter of guide tip 12. This tapered design 15, in combination with the slenderized configuration of guide tip 12 alleviates the discomfort and pain experienced by patients during insertion of large-tipped prior art tube assemblies. Unlike the insertion of large-tipped prior art tube assemblies, guide tip 12 gently parts nasal tissues and more easily slips through confined internal passages along its route into the gastrointenstinal tract of a patient. Additionally, the slenderized design of guide tip 12 prepares a path for the larger diametered bolus 14 to follow, thereby alleviating patient discomfort. Progression of the bolus 14 and tube 16 is further facilitated by the tapered distal end of the bolus 14.

Figure 3:
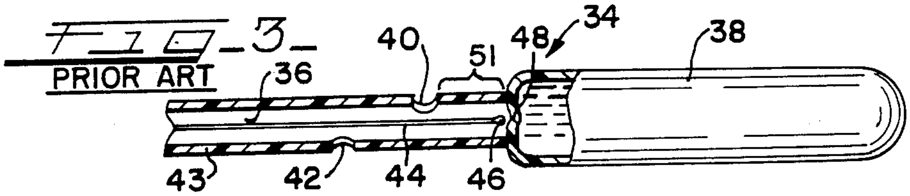
FIG. 3 PRIOR ART
FIG. 3 is a detailed cross sectional fragmentary view of a large tipped feeding tube assembly known in the art showing an inserted stylet also known in the art.

FIG. 3 illustrates a feeding tube assembly used in the art and generally referenced by the numeral 34. A brief explanation of prior art tube assemblies will make evident that the present invention represents an improvement in the method of inserting such prior art feeding assemblies having large diametered guide tips and/or apertures near the distal end of the tube. Feeding tube assembly 34 includes a tube 36 and an elongated tip 38. Tube 36 possesses staggered apertures exemplified by 40 and 42 in the tube wall 43. The apertures 40 and 42 allow for the exit of fluids from the tube 36. Apertures 40, 42 weaken the tube wall 43, thereby increasing the likelihood of the tube walls collapsing, twisting or bending and interfering with the regular flow or intake of fluids and/or the progression of tube assembly 34 during insertion. The absence of apertures in the feeding tube 16 strengthens and increases the rigidity of the tube walls, decreasing the probability of a tube folding or kinking. In addition, the absence of tubal apertures in the preferred tube assembly 10 eliminates injury to the patient by preventing escape of the stylet from the tube walls during stylet intubation.

Tip 38 is of a generally tubular shape and possesses a cross sectional diameter substantially larger than the cross sectional diameter of the tube 36. Due to its increased size, the tip 38 causes the patient to experience varying degrees of pain during insertion. Tip 38 contains liquid mercury to increase the gravitational effect during insertion of the feeding tube assembly 34. The stylet 44 shown inserted in tube 36 is used to introduce and guide the feeding tube assembly 34 through the nasal passages and into the gastrointestinal tract when peristaltic intubation is not feasible. Stylet 44 is a thin wire, known in the prior art, which contains a spherical bead 46 located at its distal end. Located at the proximal end of the tip 38 is a receiving pocket 48. The receiving pocket 48 seeks to aid in the proper placement of the spherical bead 46 and is designed to attempt to prevent the stylet 44 from exiting the apertures 40 and 42 found in the tube 36. A pocket 51 is formed in the tube 36 thereby accumulating fluids and preventing such fluids from exiting the tube 36 from either apertures 40, 42.

FIGS. 4 and 5 disclose the structure of the preferred feeding assembly 10. The tube 16 is connected to the bolus 14 with the distal end of tube 16 being inserted into an axial opening in bolus 14 and suitably sealed therein. A cylindrical channel 22 is formed at the distal end of the tube 16 within the bolus 14 in axial alignment with tube 16. A transverse cylindrical channel 24 located in bolus 14 lies perpendicular to and is in fluid communication with the cylindrical channel 22 forming a hollow "T" formation in bolus 14 allowing fluid passing through tube lumen 17 to exit the bolus 14 at openings 18 and 20; tube lumen 17 being the tubular cavity defined by the walls of tube 16. The perpendicular relationship between the channels 22, 24 of the bolus 14 eliminates the possibility of any accumulation or storage of fluids and ensures that all fluid is dispensed into the gastrointestinal tract.

The progression of any inserted stylet 26, 44 will be impeded by the top of the "T" formation and held within the rigid structure of the bolus 14, since the "T" formation in the bolus 14 acts to inhibit the stylet 26, 44 from exiting channel 24. Preferably, to facilitate the exit of fluids from the tube 16, the diameter of the channel 24 is larger than the diameter of the tube lumen 17.

FIG. 5 illustrates a stylet 26 inserted into the tube lumen 17, which is used to guide the feeding tube assembly 10 during insertion and aid in the proper placement of the feeding tube assembly 10. The stylet 26 usually is of a length greater than or equal to the length of tube 16 and is inserted into the proximal end of tube lumen 17 prior to insertion of the tube 16 into the patient. Stylet intubation of a patient is necessary whenever a patient is unable to aid the progression of the tube by swallowing or voluntary peristaltic movement.

The tubular walls 28 of the guide tip 12 shown in FIG. 5 encase cylindrical, rod-like segments 30 of a solid material which aid in the gravity placement of tube assembly 10, prevention of involuntary regurgitation of tube assembly 10, and assists in the peristaltic movement of the tube assembly into the gastrointestinal tract. Preferably, the cylindrical segments 30, 31 are composed of tungsten or a similar material which is non-toxic and essentially inert internally. The cylindrical segments 30, 31 are positioned in spaced relation with guide tip 12, and form layers of vacant space 32 between each segment. The vacant space 32 between each cylindrical segment 30, 31 enables the guide tip 12 to be flexible while simultaneously retaining some degree of rigidity. The perpendicular relationship between channels 22 and 24 of bolus 14 eliminates any accumulation or storage of fluids and ensures that all fluid is dispensed into the gastrointestinal tract.

Figure 6:
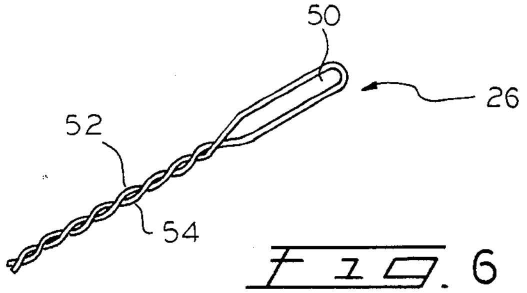
FIG. 6 is a detailed perspective view of the present invention illustrating the twisted arms and elongated loop.

FIG. 6 illustrates the subject invention generally referenced by the numeral 26. An elongated loop 50 is formed when a single strand of wire is bent in half and the resulting arms 52, 54 of the wire strand are twisted about each other yielding a double helix formation. This helix formation provides for less surface contact with the tube walls 16, 43 facilitating insertion and removal of the stylet 26 from a tube assembly. The length of the elongated loop 50 is determined by the number of twists made with the arms 52, 54 of the wire. The length and width of the elongated loop 50 may also be varied by manual manipulation once the loop 50 is formed. The rounded distal end of the elongated loop provides a smooth blunt tip which is not as likely to puncture the tube walls as the prior art stylet 44 which has a small bead at its distal end. Additionally, the maximum surface area of the tip of the new stylet 26 provides a greater contact area with the distal end of a feeding tube allowing for increased uniform forward movement of the tube assembly when force is applied to the stylet during insertion. The flexibility of the stylet 26 may also be increased or decreased by the number of twists made.

The length of the loop 50 is usually greater than the diameter of channel 24. This increased loop length decreases the possibility of the loop 50 escaping from the openings 18, 20 and injuring the patient since the loop 50 would have to bend through an angle of 90° to exit the bolus 14 through the openings 18, 20. The elongated loop 50 does not interfere with the free flow of fluids from the tube assembly 10 when fully inserted into the bolus 14.

Depending upon the curvature of the distal end of the elongated loop 50, the width of the loop 50 may be slightly less than the diameter of the feeding tube 16 or the bolus 14 "T" formation to which it is inserted. This will aid in inhibiting the stylet from escaping from the "T" formation thereby injuring the patient. Additionally, the width of the loop 50 may be adjusted so as to be greater than the major diameter of the apertures 40, 42 found in prior art tube assemblies 34, thereby preventing the stylet from escaping the tube walls 43 through the apertures 40, 42 and injuring the patient.

Figure 7:
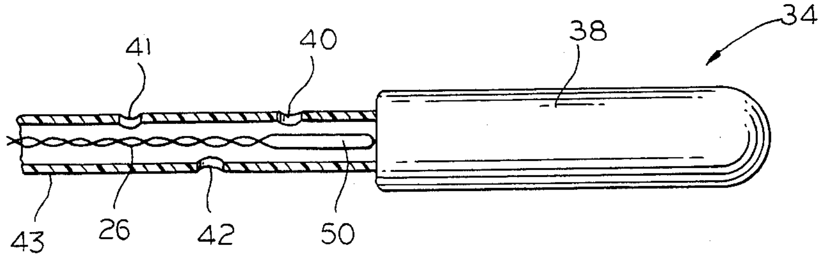
FIG. 7 is a detailed cross sectional fragmentary view of the distal end of a feeding tube assembly known in the art showing the subject invention inserted in said tube.

FIG. 7 illustrates the present invention inserted in a tube assembly 34 known in the art. The stylet 26 may be used with prior art tube assemblies, but the preferred use is with the tube assembly shown in FIGS. 2, 4, and 5, and disclosed in the patent application entitled Improved Feeding Tube Assembly. The elongated loop 50 of the stylet 26, can be made to extend past the aperture 40 thereby allowing the free flow of fluids from the aperture 40.

Figure 8:
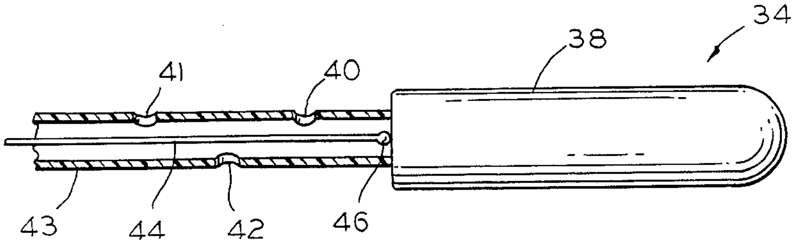
FIG. 8 (PRIOR ART)
FIG. 8 is a detailed cross sectional fragmentary view of the distal end of a feeding tube assembly known in the art showing an inserted stylet also known in the art.
Figure 9:
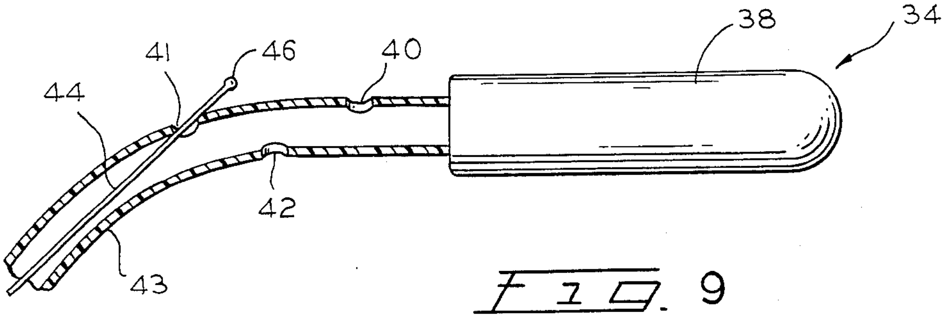
FIG. 9 (PRIOR ART)
FIG. 9 is a detailed cross sectional fragmentary view of the distal end of a partially flexed feeding tube assembly shown in FIG. 8, illustrating the escape of the stylet shown in FIG. 8 through the apertures of the tube.

FIG. 8 illustrates a stylet 44 known in the prior art as it is inserted into a prior art tube assembly 34 also shown in FIGS. 3, 7 and 9.

FIG. 9 illustrates a stylet 44 known in the prior art as it may protrude from an aperture 41 of a flexed prior art tube 36. The protrusion of the stylet 44 from the tube walls 43 can cause significant injury to a patient by scraping or puncturing the wall linings of the internal body parts which come in contact with the feeding tube during insertion (see FIG. 1). The subject invention, particularly when it is used in combination with the prefered tube assembly 10, prevents escape of the stylet 26 from the tube assembly 10, and the resulting injury to the patient.

While the invention has been described with reference to a preferred embodiment, it will be understood by those in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to a particular embodiment disclosed as the best mode contemplated for carrying out the invention, but that the invention will include all embodiments falling within the scope of the appended claims.

We claim:

1. A wire stylet for use with a feeding tube assembly for selective enteric administration and aspiration of fluids to and from the gastrointestinal tract of a patient, the assembly including a flexible tube for conducting fluids having at least one aperture in the tube wall near the distal end of said tube; and having a weighted guide tip on the distal end of said tube; said stylet including a single strand of wire insertable into said tube for aiding the insertion of said feeding tube assembly into said patient and extendable throughout the length of said tube, said wire being bent upon itself and having its two resulting ends twisted about each other simultaneously forming a double helix configuration and an elongated continuing loop at its distal end, the width of said elongated loop being slightly less than the diameter of said tube but greater than the major diameter of said apertures, whereby said loop is inhibited from exiting said apertures when guiding the tube internally, while allowing for the free flow of fluids from said tube even though said stylet remains inserted into said tube.

2. A wire stylet for use with a feeding tube assembly for selective enteric administration and aspiration of fluids to and from the gastrointestinal tract of a patient, the assembly including a flexible tube for conducting fluids; a non-collapsable contoured bolus positioned at the distal end of said tube, said bolus having a diameter greater than the diameter of said tube, said bolus having a first internal channel, said first channel being in fluid communication with said tube, said bolus having a second internal channel extending transversely to and in fluid communication with said first channel, said first channel terminating in said second channel, said second channel having oppositely faced external openings; a weighted guide tip located distal to said bolus; said stylet including a single strand of wire insertable into said tube for aiding the insertion of said feeding tube assembly into said patient and extendable throughout the length of said tube, said wire being bent upon itself and having its two resulting ends twisted about each other simultaneously forming a double helix configuration and an elongated continuing loop at its distal end, said elongated loop having its minor diameter slightly less than the diameter of said tube, said loop forming a stiffening structure of wire and having its major diameter larger than the diameter of said channels whereby said loop is inhibited from exiting said second channel, while allowing for the free flow of fluids from said bolus even though said stylet remains inserted into said bolus.

* * * * *